United States Patent [19]

Aufdermarsh, Jr.

[11] 3,963,710

[45] June 15, 1976

[54] FINELY DIVIDED BLOCKED ISOCYANATES PREPARED IN THE PRESENCE OF SURFACTANTS

[75] Inventor: Carl Albert Aufdermarsh, Jr., Newark, Del.

[73] Assignee: E. I. Du Pont de Nemours and Company, Wilmington, Del.

[22] Filed: Aug. 28, 1974

[21] Appl. No.: 501,456

[52] U.S. Cl.................. 260/247.2 A; 260/30.4 N; 260/453 AR; 260/471 C; 260/482 C; 260/858

[51] Int. Cl.$^2$..................................... C07D 295/00

[58] Field of Search................. 260/247.2 A, 471 C, 260/858

Primary Examiner—Paul J. Killos

[57] ABSTRACT

A process for the preparation of blocked polyisocyanate powders consisting of reacting the polyisocyanate and blocking agent in solution in the presence of a surfactant, whereby the product precipitates in extremely finely divided form.

11 Claims, No Drawings

FINELY DIVIDED BLOCKED ISOCYANATES PREPARED IN THE PRESENCE OF SURFACTANTS

This invention relates to an improved process for the preparation of blocked polyisocyanates in finely divided form. More particularly it is a process for the reaction of a polyisocyanate and compounds containing active hydrogen atoms under conditions such that the product precipitates as particles of extreme fineness, usually less than 10 microns in diameter.

It has been previously known to prepare solid isocyanate adducts in finely divided form by reacting an organic polyisocyanate with a blocking agent comprising an organic compound containing active hydrogen atoms as determined by the Zerewitinoff test, in a non-reactive solvent from which the product precipitates. In one such process illustrated for example in the McElroy U.S. Pat. No. 3,236,812 and the McGarr U.S. Pat. No. 3,787,525 the reaction is conducted in an inert liquid in which one of the reactants is soluble and one is insoluble. The disadvantage of this process is that it requires prior dispersion of the non-soluble material.

In another specific embodiment of the prior art, diphenylmethane-4,4'-diisocyanate (MDI) is reacted with an active hydrogen-containing compound such as phenol, resorcinol, β-naphthol, or morpholine in a mutual solvent, from which the product, a blocked polyisocyanate, precipitates as a white powder and is subsequently used in an adhesive composition for tire cord. After the adhesive is applied to a polyester tire cord, it is heated and the blocked polyisocyanate melts, dissociates, and resinifies. The smaller the particle size of the original blocked polyisocyanate is, the more uniform the resin coating and the better the adhesion. Therefore, for best adhesion performance the blocked polyisocyanate as originally isolated must be ground or micronized. Usually, it is then dispersed in water and ball-milled to effect further reduction in particle size. The disadvantage of this process is that the micronization and ball-milling add significantly to the expense of the product. It is therefore an object of this invention to eliminate those parts of the process and the corresponding expense.

This object is attained by reacting the polyisocyanate and the active hydrogen-containing compound in a mutual solvent in the presence of a selected surfactant whereupon the blocked polyisocyanate product precipitates in exceptionally finely divided form. This material, as isolated, readily disperses in water containing a wetting agent. The resulting dispersion can be used without ball-milling to prepare a polyester tire cord adhesive dip, the performance of which is as good as that of the micronized and ball-milled product now in use. By eliminating this operation, the cost of the product is significantly reduced.

The surfactants employed in this process are preferably non-ionic surfactants of the type illustrated by the olefin/vinylpyrrolidone copolymers known commercially as "Ganex" V polymers (sold by General Aniline and Film Company). These are designated by three numbers, the first number indicating the weight percent of vinylpyrrolidone in the copolymer, and the last two numbers indicating the chain length of the olefin, the latter being 3–20 carbons. For example Ganex V-816 is a copolymer containing 80% (by weight) vinylpyrrolidone and 20% hexadecene-1, while Ganex V-220 is a copolymer containing 20% vinylpyrrolidone and 80% eicosene-1. These surfactants are described in somewhat more detail in Farber U.S. Pat. No. 3,591,568 where they are said to be useful in a suspension polymerization process for the manufacture of vinyl chloride/vinyl acetate copolymers. In the present invention Ganex V-220 has been found to give the best control of particle size.

The proportions of reactants, i.e. of polyisocyanates and active hydrogen-containing compound are not critical so long as the blocking agent is present in excess, i.e. greater than stoichiometric proportions with respect to the polyisocyanate. A preferred range is 1.01–2.0 equivalents of active hydrogen-containing compound per equivalent of isocyanate group.

The reaction temperature is also not critical so long as it is below the decomposition temperature of the product. A useful range is 20° to 120°C; typically heating is under reflux conditions, for 1–4 hours.

Any suitable inert solvent may be used as long as it will dissolve the polyisocyanate and the active hydrogen-containing compound, e.g., ketones, ethers, esters, and mixtures thereof. A preferred solvent for this purpose is trichloroethylene; others which are operative include dioxane, chlorobenzene, toluene, methylene chloride, acetone, ethyl ether, and ethyl acetate.

The polyisocyanate and active hydrogen-containing compounds are not limited to those mentioned above. Aromatic polyisocyanates, being less volatile and more reactive, are preferred to aliphatic polyisocyanates. Usually, the polyisocyanates will have two -NCO groups, but isocyanates having three -NCO groups also can be used. Typical, representative, suitable polyisocyanates include, for example, toluene-2,4-diisocyanate, toluene-2,6-diisocyanate, methylenebis(4-phenyl isocyanate), triphenylmethanetriisocyanate, m-phenylenediisocyanate, polymethylenepoly(phenyl isocyanate), m-xylylenediisocyanate, and 1-chlorobenzene-2,4-diisocyanate.

The active hydrogen-containing compounds can be either primary or secondary alcohols or phenolic compounds or secondary aliphatic amines including those having the formula $HNR_1R_2$ wherein $R_1$ and $R_2$ are monovalent hydrocarbon radicals, either the same or different, containing from 1 to 30 carbon atoms and optionally also containing hetero atoms such as O, N, and S in functional groups that do not react with isocyanates or $R_1$ and $R_2$ may also form a bivalent hydrocarbon radical with the same limitations as above. Specific examples of suitable amines are: morpholine, dibutylamine, diethyl amine, etc. Specific examples of alcohols are ethanol, the primary and secondary butyl, pentyl, hexyl, etc. alcohols. The active hydrogen-containing compound may also be a mixture of the compounds recited above.

The reaction is carried out in the presence of a catalyst. Many compounds are well known to catalyze isocyanate reactions with active hydrogen-containing compounds, and many are commercially available and used, for example, in the polyurethane industry. Most commonly used catalysts, which also are suitable in the process of the present invention, include various tin compounds as well as many tertiary amines. While most tertiary amines can be used, for example, tributylamine, N-methylpiperidine, N-methylmorpholine, and such, the most efficient amine type catalyst is triethylenediamine sold under the trade name "DABCO" (Air Products and Chemicals, Inc.). Tin catalysts include, for example, dibutyltin dilaurate, stannous octoate, and stannous oleate. The amount of the catalyst is about 0.01 to 0.5% based on the weight of the reaction components, exclusive of solvent.

The following Examples are illustrative.

EXAMPLE 1

Phenol-blocked diphenylmethane-4,4'-diisocyanate prepared in the presence of a surfactant:

A flask was charged with 2200 ml. trichloroethylene and 411 g. phenol, and approximately 200 ml. trichloroethylene were distilled at atmospheric pressure to remove traces of moisture. To the flask was added approximately 24 g. of a vinylpyrrolidone (20 wt. %)/eicosene-1 (80) polymer (sold as Ganex V-220 by General Aniline and Film Co.) and 1.5 ml. diethylcyclohexylamine. The mixture was heated to 72°C. and stirred vigorously while a solution of 450 g. diphenylmethane-4,4'-diisocyanate in 500 ml. dry trichloroethylene was added. During the 30 minute addition period the temperature rose to 88.5°C and refluxing began.

A finely-divided white precipitate of phenol-blocked diphenylmethane-4,4'-diisocyanate began to form during the addition. The reaction was completed by refluxing for one hour at 88°-89°C. The slurry was cooled and suction filtered; the filter cake was washed with trichloroethylene, and then dried. The product had an average particle diameter of $2.0\mu$ by the Fisher Sub Sieve method [Ref: Carmen, P. C., and Malherbe, P. C. R., *J. Soc. Chem. Ind.* (London) 69, 134–43 (1950)].

The product was used to prepare the first dip of a tire cord adhesive as described in example 1 of U.S. patent 3,307,966 substituting sodium dioctylsulfosuccinate (sold as Aerosol OT by American Cyanamid) for the surfactant used. The dip was applied to polyester cord by means of a Litzler machine and heated one minute at 450°F.

An RFL dip was prepared as follows: A resin master is prepared by adding 2.24 pounds of 1.7% aqueous sodium hydroxide to 27.8 pounds of water at 75°-78°C., stirring for one minute, adding 1.38 pounds of resorcinol flakes slowly to the resulting solution, stirring for five minutes, adding 2.02 pounds of 37% aqueous formaldehyde, stirring for two minutes, stopping the mixing and aging the resin master at 75°-78°F. for 6 hours. The pH is 7.0 to 7.5. This resin master was added to a butadiene/styrene/2-vinyl pyridine latex with slow mixing; the RFL dip thus prepared is aged for 12 hours at 45°-50°F.

The cord was coated with the RFL dip in a Litzler machine and heated one minute at 425°F. When tested at 140°C. in rubber stock the adhesion of the cord was 50 pli in the two-ply test.

As a control for Example 1, phenol-blocked diphenylmethane-4,4'-diisocyanate was prepared in the absence of surfactant, using the same procedure and recipe as Example 1 except that Ganex V-200 was not present. The product had an average particle diameter of $7.1\mu$ by the Fisher Sub Sieve method. Polyester cord was treated with this material and tested by the procedures of Example 1. The adhesion value was 42 pli at 140°C. in the two-ply adhesion test.

EXAMPLE 2

Morpholine-blocked diphenylmethane-4,4'-diisocyanate prepared in the presence of surfactant:

A solution of 235 g. morpholine and 16 g. Ganex V-220 in 600 ml. dry trichloroethylene was added while stirring to a solution of 300 g. diphenylmethane-4,4'-diisocyanate in 600 ml. dry trichloroethylene. The temperature was controlled at 50°-70°C. during the addition period and the mixture was then heated for one hour at 60°-80°C. The product, which had separated as a finely-divided while solid, was collected by suction filtration, washed and dried. It had an average particle diameter of $6.9\mu$ by Fisher Sub Sieve method.

An adhesive was prepared and coated on polyester cord, except that the first dip was cured one minute at 450°F., as described in Example 1. When tested as described in Example 1, the cord had a two-ply adhesion value of 31 pli.

As a control for Example 2, morpholine-blocked diphenylmethane-4,4'-diisocyanate was prepared in the absence of surfactant, by the same procedure and recipe as Example 2 except that Ganex V-220 was not present. The product had an average particle diameter of $50\mu$ by the Fisher Sub Sieve Method.

When polyester cord was treated with this material in the same manner as Example 1, the two-ply adhesion was 24 pli when tested at 140°C.

EXAMPLE 3

Resorcinol- and epoxide-blocked diphenylmethane-4,4'-diisocyanate prepared in the presence of a surfactant:

A solution of 450 g. diphenylmethane-4,4'-diisocyanate, 24 g. Ganex V-220 and 0.90 ml. dibutyltin dilaurate in 1950 ml. trichloroethylene was heated to 74°C. A warm (60°C.) solution of 190 g. resorcinol, 257 g. of a glycidyl polyether of glycerol and epichlorohydrin (sold as "Epon" 812 by Shell Chemical Co.) and 100 ml. trichloroethylene was added with vigorous agitation to the isocyanate solution. The temperature rose to 88°C. and the mixture began to reflux. The product separated as a finely divided white powder. The mixture was refluxed for 1.5 hours, cooled, the product suction-filtered and dried.

It had an average particle diameter of $9.5\mu$ by the Fisher Sub Sieve method.

Polyester cord was prepared for testing by coating the cord by means of a Litzler machine at 450°F. for one minute, using a 6 wt. % aqueous emulsion (containing sodium dioctylsulfosuccinate surfactant) of the above adduct and then with the RFL dip of Example 1 for one minute at 425°F. The two-ply adhesion value in rubber stock was 55 pli.

In a control 1 for Example 3, resorcinol- and epoxide-blocked diphenylmethane-4,4'-diisocyanate was prepared in the absence of a surfactant, by the same procedure and recipe as described in Example 3 except that the Ganex V-220 was omitted. The product had an average particle diameter of $15.4\mu$ by the Fisher Sub Sieve method.

When applied to cord and tested by the same procedure as described in Example 3, the two-ply adhesion was 24 pli.

In a control 2 for Example 3, resorcinol- and epoxide-blocked diphenylmethane-4,4'-diisocyanate was prepared in the absence of surfactant, and surfactant added later. A product was prepared by the same procedure and recipe as described in the control 1 for Example 3. To one-half of the reaction mixture before isolation was added 12.0 g. Ganex V-220. After the Ganex V-220 had dissolved, the mixture was suction filtered and the product isolated and dried as above. It had an average particle diameter of 15.8μ by the Fisher Sub Sieve method.

When applied to cord and tested as in Example 3, it gave two-ply adhesion of 29 pli.

I claim:

1. A process for the preparation of finely divided blocked isocyanates consisting of reacting a polyisocyanate and an active hydrogen-containing compound, or mixture of compounds, selected from the group consisting of a primary alcohol, a secondary alcohol, a secondary amine, and a phenolic compound in solution in the presence of a surfactant, whereupon the product precipitates in exceptionally finely divided form.

2. The process of claim 1 wherein the surfactant is a nonionic surfactant.

3. The process of claim 1 wherein the surfactant is an olefin/vinylpyrrolidone copolymer.

4. The process of claim 3 wherein the surfactant is a copolymer containing 20% by weight vinylpyrrolidone and 80% by weight of eicosene-1.

5. The process of claim 1 wherein the solvent is trichloroethylene.

6. The process of claim 1 wherein the polyisocyanate is diphenylmethane-4,4'-diisocyanate, and the active hydrogen-containing compound is a phenolic compound.

7. The process of claim 6 wherein said phenolic compound is selected from the group consisting of phenol, resorcinol and naphthol.

8. The process of claim 1 wherein said active hydrogen-containing compound is a secondary aliphatic amine.

9. The process of claim 8 wherein the secondary amine is morpholine or dibutylamine.

10. The process of claim 1 wherein said active hydrogen-containing compound is a mixture of resorcinol and 2-20 equivalent wt. % of an aliphatic hydroxyl-containing material.

11. The process for the preparation of finely divided blocked polyisocyanates consisting of reacting an aromatic polyisocyanate and an active hydrogen-containing compound, or mixture of compounds, selected from a group consisting of a primary alcohol, a secondary alcohol, a secondary amine, and a phenolic compound in solution in an inert solvent containing a surfactant, whereupon the product precipitates in exceptionally finely divided form.

* * * * *